United States Patent [19]

Kraska et al.

[11] 4,025,555
[45] May 24, 1977

[54] AROMATIC AMIDINES AS ANTIVIRAL AGENTS IN ANIMALS

[75] Inventors: Allen R. Kraska, East Lyme; Rodney C. Schnur, Noank, both of Conn.

[73] Assignee: Pfizer Inc., New York, N.Y.

[22] Filed: July 23, 1976

[21] Appl. No.: 708,180

[52] U.S. Cl. .................... 260/564 R; 260/256.4 R; 260/256.4 B; 260/296 R; 260/302 R; 260/309; 260/404.5; 260/471 R; 260/501.14; 260/508; 260/509; 260/518 R; 260/518 A; 260/556 AR; 424/251; 424/263; 424/220; 424/273; 424/309; 424/312; 424/315; 424/316; 424/317; 424/324
[51] Int. Cl.² ...................... C07D 123/00
[58] Field of Search ....... 260/564 R, 501.14, 404.5, 260/556 AR, 471 R

[56] References Cited
UNITED STATES PATENTS 3,906,044   9/1975   Aigami et al. ................ 260/564 R
3,932,492   1/1976   Inamoto et al. ............... 260/564 R

OTHER PUBLICATIONS

Chemical Abstracts, vol. 56, 14163 (h) (1962).
Chemical Abstracts, vol. 41, 5137 (i) (1947).

*Primary Examiner*—Gerald A. Schwartz
*Attorney, Agent, or Firm*—Connolly and Hutz

[57] ABSTRACT

Novel [N,N-di(higher alkyl)aminomethyl]benzamidine and substituted compounds such as [N,N-di(higher alkyl)aminomethyl]-N-(2-propyl)-benzamidine and [N,N-di(higher alkyl)aminomethyl]-N-(p-hydroxyphenyl)-benzamidine and their non-toxic acid addition salts are useful for combating viral infections in vertebrate animals.

13 Claims, No Drawings

AROMATIC AMIDINES AS ANTIVIRAL AGENTS IN ANIMALS

BACKGROUND OF THE INVENTION

Virus infections which attack animals, including man, are normally contagious afflictions which are capable of causing great human suffering and economic loss. Unfortunately, the discovery of antiviral compounds is far more complicated and difficult than the discovery of antibacterial and antifungal agents. This is due, in part, to the close structural similarity of viruses and the structure of certain essential cellular components such as ribonucleic and deoxyribonucleic acids. Nevertheless, numerous non-viral "antiviral agents", i.e. substances "which can produce either a protective or therapeutic effect to the clear detectable advantage of the virus infected host, or any material that can significantly enhance antibody formation, improve antibody activity, improve non-specific resistance, speed convalescence or depress symptoms" [Herrman et al., Proc. Soc. Exptl. Biol. Med., 103, 625 (1960)], have been described in the literature. The list of reported antiviral agents includes, to name a few, interferon and synthetic materials such as amantadine hydrochloride, pyrimidines, biguanides, guanidine, pteridines and methisazone. Because of the rather narrow range of viral infections that can be treated by each of the antiviral agents commercially available at the present time, new synthetic antiviral agents are always welcomed as potentially valuable additions to the armamentarium of medical technology.

U.S. Pat. No. 3,906,044 discloses the antiviral activity of certain adamantyl amidine compounds of the formula:

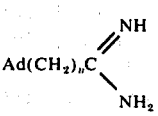

wherein $n$ is 0 or 1, and Ad is adamantyl or bridgehead carbon atom-substituted alkyladamantyl. The antiviral activity of the compound N-[bis-phenyl-(2-methoxy-5-chloro-phenyl)-methyl]-acetamidine is disclosed in British Pat. No. 1,426,603.

SUMMARY OF THE INVENTION

It has now been found that certain novel benzamidine and N-substituted benzamidine compounds are capable of combating viral infections in vertebrate animals. The novel compounds of this invention have the formula

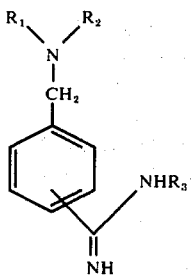

and the non-toxic acid addition salts thereof wherein $R_1$ and $R_2$ are each alkyl of from 12 to 24 carbon atoms; and $R_3$ is selected from the group consisting of hydrogen; alkyl of from one to six carbon atoms; alkenyl of from three to six carbon atoms; cycloalkyl of from three to eight carbon atoms; phenyl; phenylalkyl of from seven to nine carbon atoms; pyridyl; pyrimidyl; dimethlamino;

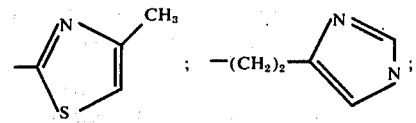

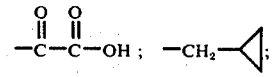

$-(CH_2)_nCH_2OH$, $-(CH_2)_nSO_3H$, and $-(CH_2)_nCF_3$, wherein $n$ is an integer of from 1 to 6; and mono— and di-substituted phenyl wherein said substituents are selected from the group consisting of fluoro, chloro, bromo, hydroxyl, nitro, trifluoromethyl, alkyl and alkoxy of from one to three carbon atoms, dimethylamino, $-N(CH_3)_3{}^+Cl^-$, $-SO_2NH_2$,

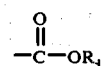

and $-SO_2R_4$, wherein $R_4$ is alkyl of from one to three carbon atoms, provided that when said phenyl ring is di-substituted at least one of said substituents is selected from the group consisting of hydroxyl, alkyl and alkoxy of from one to three carbon atoms, and dimethylamino.

The invention disclosed herein comprises the novel antiviral compounds of formula I and the novel method of treating viral infections in vertebrate animals characterized by administration of a pharmaceutical composition containing an antivirally effective amount of a compound of formula I as the essential active ingredient.

DETAILED DESCRIPTION OF THE INVENTION

The compounds of formula I exhibit prophylactic antiviral activity in vivo in vertebrate animals. It is probable that these compounds function as antiviral agents by virtue of their ability to induce the production of endogenous interferon, although the present invention is not to be construed as limited by such a theory.

By "non-toxic" acid addition salts is meant those salts which are non-toxic at the dosages administered. The non-toxic acid addition salts which may be employed include such water-soluble and water-insoluble salts as the hydrochloride, dihydrochloride, hydrobromide, phosphate, diphosphate, nitrate, sulfate, acetate, hexafluorophosphate, citrate, gluconate, benzoate, propionate, butyrate, sulfosalicylate, maleate, laurate, malate, fumarate, succinate, oxalate, tartrate, amsonate (4,4'-diaminostilbene-2,2'-disulfonate), pamoate (1,1-methylene-bis-2-hydroxy-3-naphthoate), stearate, 3-hydroxy-2-naphthoate, p-toluenesulfonate, methanesulfonate, lactate, dilactate, and suramin salts.

One preferred group of the compounds of formula I consists of the hydrochloride, dihydrochloride, hydrobromide, dihydrobromide, phosphate, diphosphate, lactate, methanesulfonate and succinate salts of the bases of formula I.

Another preferred group of the compounds of formula I consists of those wherein $R_1$ and $R_2$ are both normal alkyl.

Another preferred group of the compounds of formula I consists of those wherein $R_1$ and $R_2$ are both normal alkyl and contain the same number of carbon atoms.

Another preferred group of the compounds of formula I consists of those wherein $R_1$ and $R_2$ are both n-hexadecyl.

Another preferred group of the compounds of formula I consists of those wherein $R_1$ and $R_2$ are both n-octadecyl.

Another preferred group of the compounds of formula I consists of those wherein the benzene ring of said formula is meta-substituted.

The preferred substituents for $R_3$ are hydrogen; alkyl of from one to three carbon atoms; allyl; phenylalkyl of from seven to nine carbon atoms; dimethylamino;

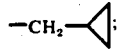

$-(CH_2)_n-SO_3H$ and $-(CH_2)_nCF_3$, wherein $n$ is an integer of from 1 to 3; and para-mono-substituted phenyl, wherein said substituent is selected from the group consisting of hydroxyl, methyl, methoxy, dimethylamino, $-N(CH_3)_3{}^+Cl^-$ and $-SO_2NH_2$.

Particularly valuable are the following compounds:

m-[N,N-di(n-hexadecyl)aminomethyl]-benzamidine,
m-[N,N-di(n-hexadecyl)aminomethyl]-N-(2-propyl)-benzamidine,
m-[N,N-di(n-hexadecyl)aminomethyl]-N-(2,2,2-trifluoroethyl)-benzamidine,
m-[N,N-di(n-hexadecyl)aminomethyl]-N-allyl-benzamidine,
m-[N,N-di(n-hexadecyl)aminomethyl]-N-dimethylamino-benzamidine,
m-[N,N-di(hexadecyl)aminomethyl]-N-(p-hydroxyphenyl)-benzamidine,
m-[N,N-di(n-hexadecyl)aminomethyl]-N-(p-methoxyphenyl)-benzamidine,
m-[N,N-di(n-hexadecyl)aminomethyl]-N-methyl-benzamidine,
m-[N,N-di(n-hexadecyl)aminomethyl]-N-(p-dimethylamino-phenyl)-benzamidine, and their non-toxic acid addition salts.

The compounds of this invention are prepared by methods familiar to those skilled in the art. The first step is generally the condensation of the appropriate α-[N,N-di(higher alkyl)amino]-toluonitrile with ethanthiol or ethanol in a hydrogen chloride saturated inert solvent such as chloroform to form the corresponding ethylthio-benzimidate or ethylbenzimidate dihydrochloride, as for example:

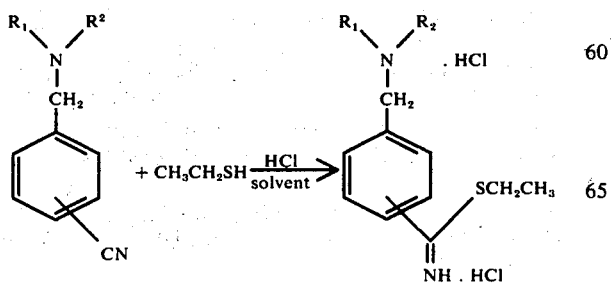

The second step is the reaction of $H_2NR_3$ with the imidate. When $R_3$ is not hydrogen and $H_2NR_3$ is not strongly basic, the second step of the preparation is the standard Pinner synthesis of amidines from imidates (Patai, S., ed., "The Chemistry of Amidines and Imidates", John Wiley and Sons, Inc., New York, 1975, pp. 283–341), i.e., the nucleophilic substitution of $-NHR_3$ for ethanthiol or ethanol in an inert solvent, e.g. chloroform, as for example:

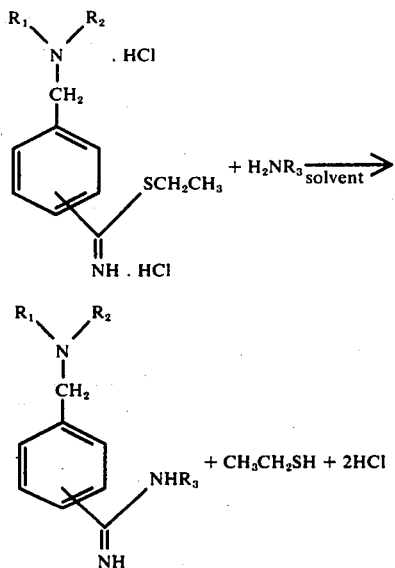

The reaction product is the desired N-substituted benzamidine.

When $R_3$ is not hydrogen and $H_2NR_3$ is strongly basic, use of the standard synthesis described above yields the nitrile rather than the amidine. Efficient production of the amidine can be achieved, however, by pH control in the region 4–9 as e.g., with acetic acid or an acetic acid/sodium acetate buffer system as described in Examples 20–33.

Compounds of formula I wherein $R_3$ is hydrogen are prepared by condensation of the appropriate α-[N,N-di(higher alkyl)amino]-toluonitrile with ethanol or ethanethiol in a hydrogen chloride saturated inert solvent such as dioxane to form the corresponding ethylbenzimidate or ethylthiobenzimidate dihydrochloride, followed by nucleophilic substitution with $NH_3$ and elimination of ethanol, or ethanethiol which is carried out in ammonia saturated ethanol. The reaction product is the desired [N,N-di(higher alkyl)aminomethyl]-benzamidine.

The compounds wherein $R_3$ is $-(CH_2)_nSO_3H$, wherein $n$ is an integer of from 1 to 6, are prepared by condensation of the appropriate [N,N-di(higher alkyl)aminomethyl]benzamidine (i.e. $R_3 = H$) with the appropriate γ-sultone or the appropriate sulfonic acid in an inert solvent, e.g., 1,2-dichloroethane. The compounds wherein $R_3$ is

are prepared in the same manner using oxalyl chloride and the appropriate benzamidine.

It is to be understood that any reaction-inert solvent may be used in place of chloroform, dioxane or 1,2-dichloroethane in any of the methods of preparation described above. The list of acceptable reaction solvents includes, but is not limited to, chloroform, dioxane, 1,2-dichloroethane, ethyl acetate and methylene chloride. Each of the reactions described above is typically performed at or near room temperature.

It is to be understood that any of the common procedures for amidine synthesis referred to in the literature reviews, such as Patai, S., ed., op. cit., arising from the appropriate intermediates such as imidates, thioimidates, iminoyl chlorides, thioamides, nitriles, amides or amidines, may be used to produce the compounds of this invention.

Acid addition salts of the bases of formula I may be prepared by conventional procedures such as by mixing the amidine compound in a suitable solvent with the required acid and recovering the salt by evaporation or by precipitation upon adding a non-solvent for the salt. Hydrochloride salts may readily be prepared by passing dry hydrogen chloride through a solution of the amidine compound in an organic solvent.

The α-[N,N-di(higher alkyl)amino]-toluonitriles used as starting materials may be prepared by contacting α-bromotoluonitrile with an appropriate N,N-di(higher alkyl)amine in dimethylacetamide in the presence of potassium carbonate. α-Bromotoluonitrile is an article of commerce obtainable, for example, from Shawnee Chemicals. The N,N-di(higher alkyl)amine is obtained by refluxing a (higher alkyl) amine with the appropriate carboxylic acid in a suitable solvent such as xylene and then contacting the N-(higher alkyl)amide which is formed with sodium bis(2-methoxyethoxy)-aluminum hydride in a suitable solvent such as benzene to produce the desired N,N-di(higher alkyl)amine. Sodium bis-(2-methoxy-ethoxy)aluminum hydride is an article of commerce obtainable, for example from Eastman Kodak Corporation as a 70% solution in benzene under the trade name of Vitride. As will easily be recognized by those skilled in the art, this procedure may be employed to prepare N,N-di(higher alkyl)amines in which the alkyl groups are either identical or different. If an N,N-di(higher alkyl)amine with identical alkyl groups is desired, a process comprising refluxing the mono-(higher alkyl)-amine in a suitable solvent such as toluene in the presence of Raney nickel catalyst to produce the desired N,N-di(higher alkyl)-amine may also be employed. This latter process is not in common use because tertiary amines, which are typically difficult to separate from the desired secondary amine product, are frequently formed. This problem is not serious, however, when the alkyl groups are higher alkyl (i.e., 12 to 24 carbon atoms), because of the apparent steric hindrance to tertiary amine formation afforded by the great bulk of the alkyl moieties and the ease of separating tertiary from secondary (higher alkyl)amines.

The antiviral activity of the compounds of formula I is determined by the following procedure. The test compound is administered to mice by the intraperitoneal route 18 to 24 hours prior to challenging them with a lethal dose of encephalomyocarditis (EMC) virus. The survival rate is determined 10 days after challenge and an $ED_{50}$ [dosage level (mg of compound/kg body weight) required to obtain a 50 percent survival rate] calculated. The procedure in which the drug is given 18 to 24 hours before, and at a distinctly different site from, virus injection is designed to eliminate local effects between drug and virus and identify only those compounds which produce a systemic antiviral response.

Certain of the compounds of formula I were also tested for their ability to induce circulating interferon in mice after parenteral administration, using the procedure described by Hoffman, W. W. et al., Antimicrobial Agents and Chemotherapy, 3, 498–501 (1973).

Parenteral, topical and intranasal administration of the above-described amidines to an animal before exposure of the animal to an infectious virus provide rapid resistance to the virus. Such administration is effective when given as much as 5 days prior to exposure to the virus. Preferably, however, administration should take place from about 3 days to about 1 day before exposure to the virus, although this will vary somewhat with the particular animal species and the particular infectious virus.

When administered parenterally (subcutaneously, intramuscularly, intraperitoneally) the materials of this invention are used at a level of from about 1 mg./kg. of body weight to about 250 mg./kg. body weight. The favored range is from about 5 mg./kg. to about 100 mg./kg. of body weight, and the preferred range from about 5 mg. to about 50 mg./kg. of body weight. The dosage, of course, is dependent upon the animal being treated and the particular amidine compound involved and is to be determined by the individual responsible for its administration. Generally, small doses will be administered initially with gradual increase in dosage until the optimal dosage level is determined for the particular subject under treatment.

Vehicles suitable for parenteral injection may be either aqueous such as water, isotonic saline, isotonic dextrose, Ringer's solution, or non-aqueous such as fatty oils of vegetable origin (cottonseed, peanut oil, corn, sesame) and other non-aqueous vehicles which will not interfere with the efficacy of the preparation and are non-toxic in the volume or proportion used (glycerol, ethanol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol.

When the materials of this invention are administered, they are most easily and economically used in a dispersed form in an acceptable carrier. When it is said that this material is dispersed, it means that the particles may be molecular in size and held in true solution in a suitable solvent or that the particles may be colloidal in size and dispersed through a liquid phase in the form of a suspension or an emulsion. The term "dispersed" also means that the particles may be mixed with and spread throughout a solid carrier so that the mixture is in the form of a powder or dust. This term is also meant to encompass mixtures which are suitable for use as sprays, including solutions, suspensions or emulsions of the agents of this invention.

In practicing the intranasal route of administration of this invention any practical method can be used to contact the antiviral agent with the respiratory tract of the animal. Effective methods include administration of the agent by intranasal or nasopharyngeal drops and by inhalation as delivered by a nebulizer or an aerosol. Such methods of administration are of practical importance because they provide an easy, safe and efficient

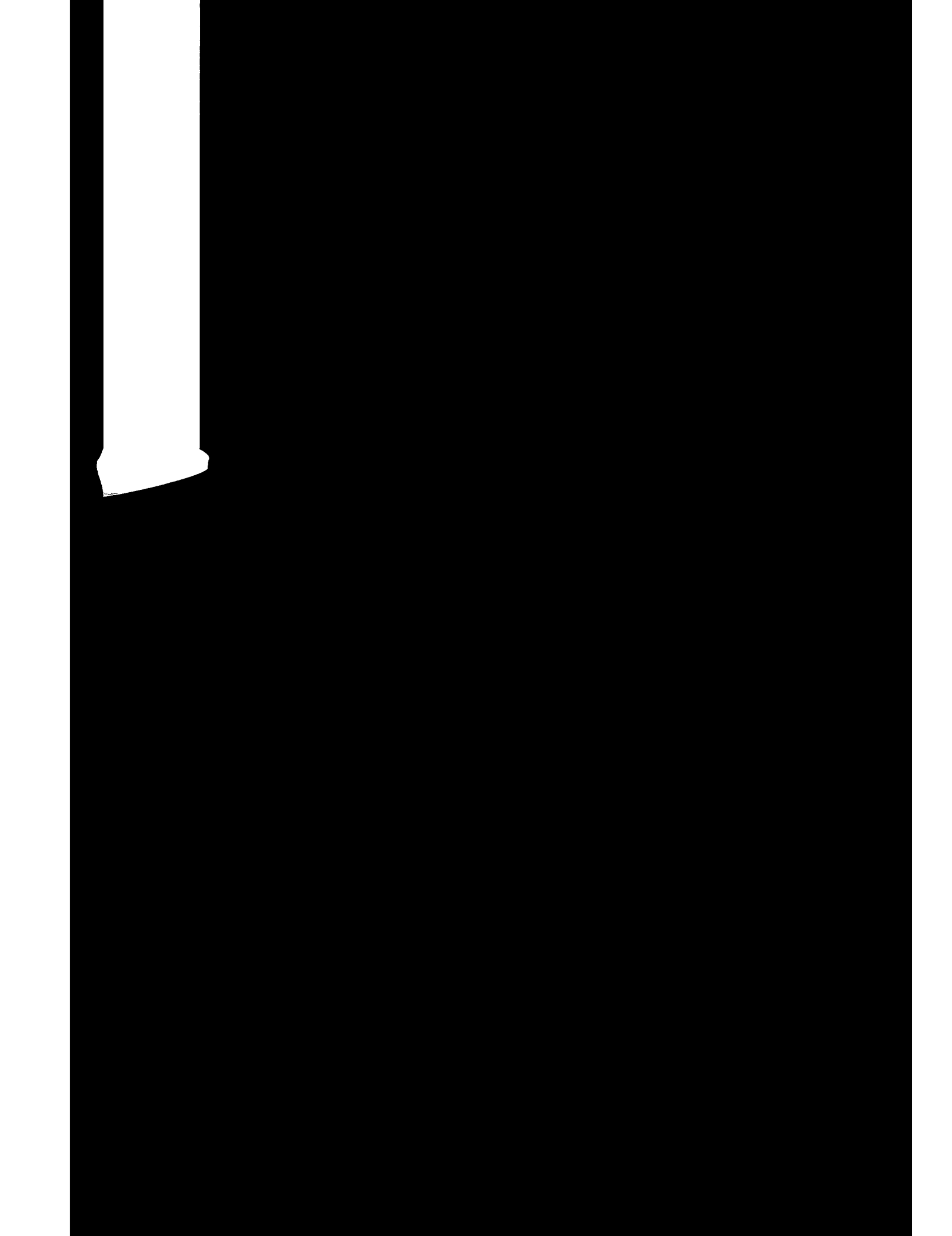

EXAMPLE 4 m-[N,N-Di(n-hexadecyl)aminomethyl]-N-oxoacetic acid-benzamidine

In like manner to that described in Example 3 the compound m-[N,N-di-(n-hexadecyl)aminomethyl]-N-oxoacetic acid-benzamidine was prepared by using oxalyl chloride as starting material and a reaction time of 1.5 hours. The oil was crystallized from 1,2-dimethoxyethane [34% yield, $R_f$ .31 (4:1, benzene:ethanol on silicic acid), m.p.-forms a gel at 97°–105° C.].

EXAMPLE 5

Ethyl-m-[N,N-di(n-hexadecyl)aminomethyl]-thiobenzimidate Dihydrochloride

A mixture of α-[N,N-di(n-hexadecyl)amino]-m-toluonitrile (23.2 g., 0.04 mole), ethanthiol (6.0 ml., 0.08 mole) and chloroform (100 ml.) was saturated with dry hydrogen chloride for 30 minutes at 20°–25° C. It was then stoppered and held for 6 days at 5° C. The mixture was evaporated in vacuo to a foam which was crystallized by trituration with 1,2-dimethoxyethane. The crude product was recrystallized from hot 1,2-dimethoxyethane/chloroform [24.9 g., 88% yield, $R_f$ 0.79 (4:1, benzene:ethanol on silicic acid), m.p. 109°–111° C.].

EXAMPLE 6 m-[N,N-Di(n-hexadecyl)aminomethyl]-N-(p-methoxyphenyl)-benzamidine

A mixture of ethyl-m-[N,N-di(n-hexadecyl)aminomethyl]-thiobenzimidate dihydrochloride (1.074 g., 1.5 mmoles), p-anisidine (369 mg., 3.0 mmoles) and chloroform (10 ml.) was held at room temperature for 16 hours. It was then diluted to 400 ml. with chloroform, washed with 1N HCl (2 × 50 ml.), dried ($Na_2SO_4$) and evaporated in vacuo to a foam. The foam was crystallized from 1,2-dimethoxyethane [868 mg., 73% yield, $R_f$ .64 (4:1, benzene:ethanol on silicic acid), m.p.-forms a gel at 84°–86° C.].

EXAMPLES 7–19

In like manner to that described in Example 6 the following compounds were prepared by using appropriate reactants ($H_2N$—$R_3$) in place of p-anisidine:

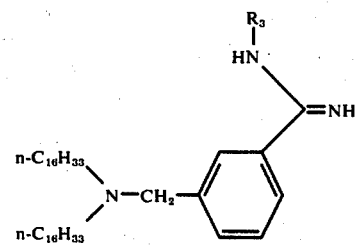

| Example Number | $R_3$ | Reaction Time (hrs.) | Yield (%) | Crystallization Solvent System[a] | M.P. (° C) | $R_f$[b] |
|---|---|---|---|---|---|---|
| 7 | —⟨phenyl⟩ | 16 | 88 | DME | 86–88[d] | .50 |
| 8 | —⟨C₆H₄⟩—Cl | 16 | 88 | DME | 135–137 | .47 |
| 9 | —⟨C₆H₄⟩—CH₃ | 16 | 73 | DME | 164–167 | .69 |
| 10 | —⟨pyridyl⟩ | 16 | 67 | DME | 156–157 | .73 |
| 11 | —⟨C₆H₃⟩(Cl)(Cl) | 48 | 19 | DME/CH₃CN | 85–87[d] | .83 |
| 12 | —⟨C₆H₄⟩—OH | 48 | 59 | DME/CHCl₃ | 125[d] | .24 |

-continued

| Example Number | R₃ | Reaction Time (hrs.) | Yield (%) | Crystallization Solvent System[a] | M.P. (° C) | R_f[b] |
|---|---|---|---|---|---|---|
| 13 | -C₆H₄-NO₂ (m) | 48 | 62 | DME | 152–154 | .76 |
| 14 | -C₆H₄-N(CH₃)₂ (p) | 3 | 83 | DME | 167 | .37 |
| 15 | -C₆H₄-F (p) | 48 | 68 | DME | 91–92[d] | .69 |
| 16 | -C₆H₄-SO₂NH₂ (p) | 48 | 89 | DME/CHCl₃ | 164[d] | .78 |
| 17 | pyrimidin-2-yl | 36[c] | 8 | DME | 128[d] | .70 |
| 18 | -C₆H₄-OCH₂CH₃ (p) | 0.5 | 90 | DME | 167–169 | .55 |
| 19 | -C₆H₄-SO₂CH₃ (p) | 48 | 15 | Acetone | 75[d] | .69 |

[a] - DME ≡ 1,2-dimethoxyethane; CH₃CN ≡ acetonitrile; CHCl₃ ≡ chloroform
[b] - 4:1, benzene:ethanol on silicic acid
[c] - reaction carried out at reflux
[d] - forms a gel

EXAMPLE 20 m-[N,N-Di(n-hexadecyl)aminomethyl]-N-cyclopentyl-benzamidine

Ethyl-m-[N,N-di(n-hexadecyl)aminomethyl]-thiobenzimidate dihydrochloride (1.074 g., 1.5 mmoles) was added to a solution of cyclopentylamine (255 mg., 3.0 mmoles), glacial acetic acid (0.3 ml., 5.3 mmoles) and chloroform (10 ml.). The mixture was held for 72 hours at room temperature. It was then diluted to 300 ml. with chloroform, washed with saturated aqueous sodium bicarbonate solution (3 × 50 ml.), washed with saturated aqueous sodium chloride solution (3 × 50 ml.), dried (Na₂SO₄) and filtered. The filtrate was acidified with a 10% solution of anhydrous hydrogen chloride in dioxane (5 ml.) and then evaporated in vacuo to an oil. The oil was crystallized from warm 1,2-dimethoxyethane [850 mg., 77% yield, R_f .30 (4:1, benzene:ethanol on silicic acid), m.p.-forms a gel at 78° C.].

EXAMPLES 21–27

In like manner to that described in Example 20 the following compounds were prepared by using appropriate reactants (H₂N—R₃) in place of cyclopentylamine:

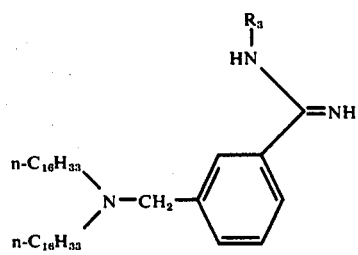

| Example Number | R₃ | Reaction Time (hrs.) | Yield (%) | Crystallization Solvent System[a] | M.P. (°C) | R_f[b] |
|---|---|---|---|---|---|---|
| 21 | (4-methyl-thiazol-2-yl) | 48 | 28 | DME | 172–176 | .75 |
| 22 | —CH₂—C₆H₅ | 1.5 | 88 | DME | 154–157 | .37 |
| 23 | —N(CH₃)₂ | 16 | 23 | DME/CH₃CN | 82[d] | .38 |
| 24 | —CH₂CH=CH₂ | 16 | 77 | DME/CH₃CN | 70[d] | .29 |
| 25 | —CH(CH₃)₂ | 48 | 55 | DME | 95[d] | .30 |
| 26 | —CH₂CH₃[c] | 72 | 84 | DME | 91[d] | .22 |
| 27 | —CH₃[c] | 72 | 90 | DME | 106[d] | .18 |

[a] - DME≡1,2-dimethoxyethane; CH₃CN≡acetonitrile
[b] - 4:1, benzene:ethanol on silicic acid
[c] - ethylamine (methylamine) bubbled as a gas into acetic acid:chloroform solution
[d] - forms a gel

EXAMPLE 28 m-[N,N-Di(n-hexadecyl)aminomethyl]-N-(2,2,2-trifluoroethyl)-benzamidine

Ethyl-m-[N,N-di(n-hexadecyl)aminomethyl]-thiobenzimidate dihydrochloride (1.074 g., 1.5 mmoles) was added to a slurry of 2,2,2-trifluoroethylamine hydrochloride (406 mg., 3.0 mmoles) and anhydrous sodium acetate (246 mmoles) in chloroform (10 ml.) and glacial acetic acid (0.3 ml., 5.3 mmoles). The mixture was held for 12 hours at room temperature. It was then diluted to 300 ml. with chloroform, washed with saturated aqueous sodium bicarbonate solution (2 × 50 ml.), washed with saturated aqueous sodium chloride solution (2 × 50 ml.), dried (Na₂SO₄) and filtered. The filtrate was acidified with a 10% solution of anhydrous hydrogen chloride in dioxane (5 ml.) and then evaporated in vacuo to a foam. The foam was crystallized from 1,2-dimethoxyethane [974 mg., 86% yield, R_f .39 (4:1, benzene: ethanol on silicic acid), m.p.-forms a gel at 125°–127° C.].

EXAMPLES 29–33

In like manner to that described in Example 28 the following compounds were prepared by using appropriate reactants (H₂N—R₃.HCl) in place of 2,2,2-trifluoroethylamine hydrochloride:

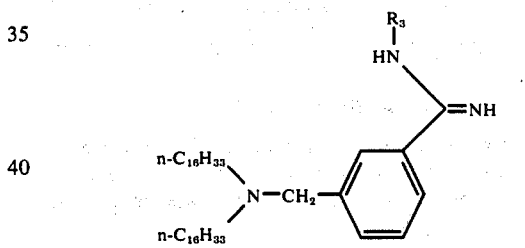

| Example Number | R₃ | Reaction Time (hrs.) | Yield (%) | Crystallization Solvent System[a] | M.P. (°C) | R_f[b] |
|---|---|---|---|---|---|---|
| 29 | —CH₂-cyclopropyl | 24 | 57 | DME | 77–79[c] | .43 |
| 30 | (4-hydroxy-3-methylphenyl) | 48 | 60 | DME/CH₃CN | 115–118[c] | .46 |
| 31 | —CH₂CH₂-(imidazolyl) | 16 | 29 | DME | 238[c] | .60 |
| 32 | (4-N(CH₃)₃⁺Cl⁻-phenyl) | 3 | 55 | DME/CHCl₃ | 163–166 | .00 |

-continued

| Example Number | R₃ | Reaction Time (hrs.) | Yield (%) | Crystallization Solvent System[a] | M.P. (°C) | $R_f$[b] |
|---|---|---|---|---|---|---|
| 33 | 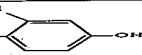 | 24 | 40 | DME/water | 140[c] | .27 |

[a] - DME≡1,2-dimethoxyethane; CH₃CN≡acetonitrile; CHCl₃≡chloroform
[b] - 4:1, benzene:ethanol on silicic acid
[c] - forms a gel

EXAMPLES 34–35

In like manner to that described in Examples 3–4 the following compounds may be prepared by using appropriate reactants in place of 3-hydroxy-1-propanesulf -continued

| Example Number | R₅ |
|---|---|

-continued

-continued

| Example Number | $R_6$ | $R_7$ |
|---|---|---|
| 78 | chloro | dimethylamino |
| 79 | methyl | methyl |
| 80 | methyl | methoxy |
| 81 | 2-propyl | dimethylamino |
| 82 | methoxy | dimethylamino |
| 83 | 1-propyloxy | —SO$_2$(CH$_2$)$_2$CH$_3$ |
| 84 | ethyl | —SO$_2$NH$_2$ |
| 85 | ethoxy | —(CO)OCH(CH$_3$)$_2$ |
| 86 | 1-propyl | —(CO)OCH$_3$ |
| 87 | dimethylamino | dimethylamino |
| 88 | 2-propyloxy | dimethylamino |
| 89 | dimethylamino | —SO$_2$NH$_2$ |
| 90 | dimethylamino | —SO$_2$CH$_3$ |
| 91 | dimethylamino | —(CO)OCH$_3$ |
| 92 | dimethylamino | —(CO)O(CH$_2$)$_2$CH$_3$ |

EXAMPLES 93–98

In like manner to that described in Examples 20–27 the following compounds may be prepared by using appropriate reactants (H$_2$N—R$_3$) in place of cyclopentylamine:

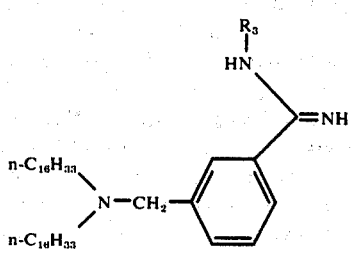

| Example Number | $R_3$ |
|---|---|
| 93 | n-hexyl |
| 94 | 2-butenyl |
| 95 | 2-hexenyl |
| 96 | cyclopropyl |
| 97 | cyclooctyl |
| 98 | phenyl (1-propyl) |

EXAMPLES 99–103

In like manner to that described in Examples 28–33 the following compounds may be prepared by using appropriate reactants (H$_2$NR$_3$·HCl) in place of 2,2,2-trifluoroethylamine hydrochloride:

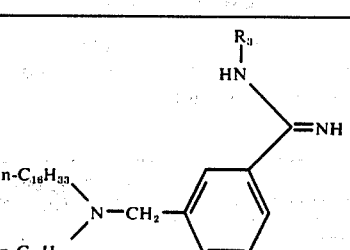

| Example Number | $R_3$ |
|---|---|
| 99 | —(CH$_2$)$_2$OH |
| 100 | —(CH$_2$)$_7$OH |
| 101 | —(CH$_2$)$_6$CF$_3$ |
| 102 | N(CH$_3$)$_3$$^+$Cl$^-$ (phenyl) |
| 103 | N(CH$_3$)$_3$$^+$Cl$^-$ (benzyl) |

EXAMPLES 104–112

In like manner to that described in Examples 28–33 the following compounds may be prepared by using appropriate reactants (H$_2$NR$_3$·HCl) in place of 2,2,2-trifluoroethylamine hydrochloride:

| Example Number | $R_6$ | $R_7$ |
|---|---|---|
| 104 | hydroxyl | chloro |
| 105 | hydroxyl | methoxy |
| 106 | hydroxyl | dimethylamino |
| 107 | hydroxyl | —SO$_2$NH$_2$ |
| 108 | hydroxyl | —(CO)OCH$_3$ |
| 109 | hydroxyl | —N(CH$_3$)$_3$$^+$Cl$^-$ |
| 110 | —N(CH$_3$)$_3$$^+$Cl$^-$ | methyl |
| 111 | —N(CH$_3$)$_3$$^+$Cl$^-$ | dimethylamino |
| 112 | hydroxyl | ethyl |

EXAMPLE 113

Antiviral Activity of m-[N,N-di(n-hexadecyl)aminomethyl]-N-allylbenzamidine Dihydrochloride Three groups of 10 female albino mice (20–25 g. body weight) were given single 0.5 ml. intraperitoneal injections containing dosage levels of 1.5, 5, and 15 mg. of the named compound/kg. body weight, respectively. A fourth control group was given no such injection.

Eighteen to 24 hours later all four groups were challenged with a 0.2 ml. subcutaneous injection containing 20–30 times the $LD_{50}$, the dosage level causing a 50% death rate in 10 days, of encephalomyocarditis (EMC) virus. The following survival data were recorded for the following 10 days:

| Dosage Level of Named Compound | Number of Survivors on Day Number | | | | | | | | | | | $S_r$ |
|---|---|---|---|---|---|---|---|---|---|---|---|---|
| | 0 | 1 | 2 | 3 | 4 | 5 | 6 | 7 | 8 | 9 | 10 | |
| 15 mg./kg. | 10 | 10 | 10 | 10 | 9 | 8 | 8 | 8 | 8 | 8 | 8 | 80 |
| 5 | 10 | 10 | 10 | 10 | 10 | 6 | 6 | 6 | 5 | 5 | 5 | 53 |
| 1.5 | 10 | 10 | 10 | 10 | 9 | 5 | 4 | 2 | 2 | 2 | 1 | 19 |
| 0 (control) | 10 | 10 | 10 | 9 | 3 | 1 | 1 | 0 | 0 | 0 | 0 | — |

Antiviral activity is expressed as the relative survival ($S_r$) in experimental groups compared to the controls on the tenth day after challenge. $S_r$ is defined by the formula $$S_r = \left[ \frac{S_r + \sum_{i=1 \text{ to } 10} x_i - \sum_{i=1 \text{ to } 10} e_i}{100 + 100 - \sum_{i=1 \text{ to } 10} e_i} \right] \times 100$$

wherein
- $S_r$ = relative survival
- $S_x$ = percent survival after 10 days in experimental group
- $x_i$ = number of survivors on the $i$th day in experimental group
- $e_i$ = number of survivors on the $i$th day in control group The $ED_{50}$ [dosage level (mg. of compound/kg. body weight) required to obtain a 50 percent survival rate] is determined graphically by plotting $S_r$ (ordinate) vs. $\ln$ dosage level (abscissa) and then fitting the points with a line of predetermined slope by least squares. The dosage level at which this fitted line has an ordinate of 50 is equivalent to the $ED_{50}$.

This graphical method was used to determine an $ED_{50}$ for the named compound of 4.7 mg. (as dihydrochloride salt)/kg.

EXAMPLES 114–143

In like manner to that described in Example 113 the antiviral activity was determined for the compounds listed below.

| Example Number | Compound Prepared in Example Number | $ED_{50}$(mg./kg.)[a] |
|---|---|---|
| 114 | 2 | 4.7 |
| 115 | 3 | 8.0 |
| 116 | 4 | 9.9 |
| 117 | 6 | 5.3 |
| 118 | 7 | 12.3 |
| 119 | 8 | 16.0 |
| 120 | 9 | 7.7 |
| 121 | 10 | 49.3 |
| 122 | 11 | 35.7 |
| 123 | 12 | 4.9 |
| 124 | 13 | 21.6 |
| 125 | 14 | 8.0 |
| 126 | 15 | 38.0 |
| 127 | 16 | 7.0 |
| 128 | 17 | 12.9 |
| 129 | 18 | 17.9 |
| 130 | 19 | 8.9 |
| 131 | 20 | 27.3 |
| 132 | 21 | 47.5 |
| 133 | 22 | 7.8 |
| 134 | 23 | 5.0 |
| 135 | 25 | 2.8 |
| 136 | 26 | 7.6 |
| 137 | 27 | 5.7 |
| 138 | 28 | 3.8 |
| 139 | 29 | 6.9 |
| 140 | 30 | 7.7 |
| 141 | 31 | 11.7 |
| 142 | 32 | 7.4 |
| 143 | 33 | 37.2 |

[a]all as mg. dihydrochloride salt except for Example 115 (mg. free base)

EXAMPLE 144

Ability of m-[N,N-di(n-hexadecyl)aminomethyl]-N-(p-hydroxyphenyl)-benzamidine to Induce Circulating Interferon A quantity of the named compound was fused with equal weights of polysorbate 80 and glycerol. The mixture was then homogenized in hot 0.14 M NaCl containing 0.01 sodium phosphate, pH 7 (PBS). The resulting oil-in-water emulsion was readily diluted with PBS.

Female Swiss mice (20–25 g. body weight) were injected (intraperitoneal) with an amount of the above diluted emulsion containing 25 mg. of the named compound/kg. body weight. 8, 12, 16 and 20 hours after injection samples of plasma were withdrawn from the mice. These samples were then serially diluted. L-929 mouse fibroblasts were incubated on microtiter plates with aliquots of the various samples of serially diluted plasma for 18 hours at 37° C. The fibroblast monolayers were then washed with protein-free medium and challenged with 10–40 times the $TCID_{50}$, the dose in which 50% of the cultures are infected, of vesicular stomatitis virus (VSV). The virus was allowed to absorb for 1 hour at 37° C. before addition of 0.2 ml. of maintenance medium. The cultures were scored and analyzed about 24 to 48 hours later and the plasma interferon level, the reciprocal of the plasma dilution at which 50 percent of the cultures are protected, determined. The following data were obtained.

| Plasma Interferon Levels (units/ml.) | | | |
|---|---|---|---|
| Time (hrs.) after Injection | | | |
| 8 | 12 | 16 | 20 |
| 102 | 276 | 143 | 76 |

EXAMPLES 145–150

In like manner to that described in Example 144 the ability to induce circulating interferon was determined for the compounds listed below.

| Ex. No. | Compound Prepared in Example Number | Plasma Interferon Levels (units/ml.) | | | |
|---|---|---|---|---|---|
| | | Time (hrs.) after Injection | | | |
| | | 8 | 12 | 16 | 20 |
| 145 | 2 | 76 | 116 | 56 | 48 |
| 146 | 24 | 26 | 60 | 110 | 102 |
| 147 | 25 | <17 | 114 | 34 | 154 |
| 148 | 27 | 37 | 95 | 100 | 71 |
| 149 | 28 | 38 | 160 | 126 | 49 |
| 150 | 30 | 66 | 87 | 61 | 64 |

EXAMPLE 151

Compounds wherein $R_1$ and $R_2$ are not both n-(hexadecyl) and/or the phenyl ring of formula I is not meta-substituted may be prepared in like manner as described in Examples 1-33 for the corresponding m-[N,N-di(n-hexadecyl)] compounds by using the appropriate starting materials, and tested for antiviral activity in like manner as described in Example 113.

What is claimed is:

1. A compound of the structure

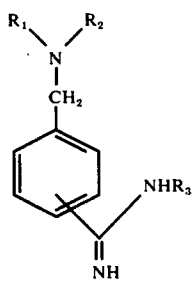

and the non-toxic acid addition salts thereof wherein
$R_1$ and $R_2$ are each alkyl of from 12 to 24 carbon atoms; and
$R_3$ is selected from the group consisting of hydrogen; alkyl of from one to six carbon atoms; alkenyl of from three to six carbon atoms; cycloalkyl of from three to eight carbon atoms; phenyl; phenylalkyl of from seven to nine carbon atoms;

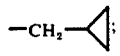

and mono- and di-substituted phenyl wherein said substituents are selected from the group consisting of fluoro, chloro, bromo, hydroxyl, nitro, trifluoromethyl, alkyl and alkoxy of from one to three carbon atoms, dimethylamino, $-N(CH_3)_3{}^+Cl^-$, $-SO_2NH_2$,

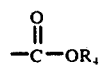

and $-SO_2R_4$, wherein $R_4$ is selected from the group consisting of alkyl of from one to three carbon atoms, provided that when said phenyl ring is di-substituted at least one of said substituents is selected from the group consisting of hydroxyl, alkyl and alkoxy of from one to three carbon atoms, and dimethylamino.

2. A compound of claim 1 wherein $R_1$ and $R_2$ are normal alkyl.

3. A compound of claim 2 wherein $R_1$ and $R_2$ have an equal number of carbon atoms.

4. A compound of claim 1 wherein $R_1$ and $R_2$ are n-hexadecyl.

5. A compound of claim 1 wherein $R_1$ and $R_2$ are n-octadecyl.

6. A compound of claim 1 wherein the benzene ring of said structure is meta substituted.

7. A compound of claim 1 wherein $R_1$ and $R_2$ are n-hexadecyl and the benzene ring of said structure is meta substituted.

8. A compound of claim 1 wherein $R_3$ is selected from the group consisting of hydrogen; alkyl of from one to three carbon atoms; allyl; phenylalkyl of from seven to nine carbon atoms;

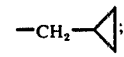

and para-mono-substituted phenyl, wherein said substituent is selected from the group consisting of hydroxyl, methyl, methoxy, dimethylamino, $-N(CH_3)_3{}^+Cl^-$ and $-SO_2NH_2$.

9. A compound of claim 7 wherein $R_3$ is hydrogen.

10. A compound of claim 7 wherein $R_3$ is allyl.

11. A compound of claim 7 wherein $R_3$ is 2-propyl.

12. A compound of claim 7 wherein $R_3$ is p-hydroxyphenyl.

13. A compound of claim 7 wherein $R_3$ is p-dimethylaminophenyl.

* * * * *